US007842014B2

(12) United States Patent
Schweitzer et al.

(10) Patent No.: US 7,842,014 B2
(45) Date of Patent: Nov. 30, 2010

(54) SURGICAL SEALING ELEMENT, SURGICAL SEAL, AND SURGICAL SEALING SYSTEM

(75) Inventors: Tom Schweitzer, Tuttlingen (DE); Rupert Mayenberger, Rielasingen (DE)

(73) Assignee: Aesculap AG, Tuttlingen (DE)

( * ) Notice: Subject to any disclaimer, the term of this patent is extended or adjusted under 35 U.S.C. 154(b) by 162 days.

(21) Appl. No.: 12/283,132

(22) Filed: Sep. 8, 2008

(65) Prior Publication Data
US 2009/0082735 A1 Mar. 26, 2009

Related U.S. Application Data

(63) Continuation of application No. PCT/EP2007/052760, filed on Mar. 22, 2007.

(30) Foreign Application Priority Data

Mar. 27, 2006 (DE) ............... 10 2006 015 690

(51) Int. Cl.
*A61M 5/178* (2006.01)
*A61M 5/315* (2006.01)
(52) U.S. Cl. .................. 604/167.06; 604/236
(58) Field of Classification Search .................
604/167.01–167.03, 167.06, 236–237, 524, 604/526, 530
See application file for complete search history.

(56) References Cited

U.S. PATENT DOCUMENTS

| 3,712,298 | A | | 1/1973 | Snowdon et al. |
| 3,845,766 | A | * | 11/1974 | Zoller .................. 604/330 |
| 4,265,694 | A | | 5/1981 | Boretos et al. |
| 5,104,382 | A | | 4/1992 | Brinkerhoff et al. |
| 5,114,407 | A | | 5/1992 | Burbank |

(Continued)

FOREIGN PATENT DOCUMENTS

CA 2 504 540 4/2005

(Continued)

OTHER PUBLICATIONS

Aesculap brochure, "MIT-System, Multi Interchangeable Trocar-System", 3 pages (undated).

*Primary Examiner*—Nicholas D Lucchesi
*Assistant Examiner*—Rebecca E Eisenberg
(74) *Attorney, Agent, or Firm*—Lipsitz & McAllister, LLC (57) ABSTRACT

In order to improve a surgical sealing element, in particular, for a trocar and/or for sealing shafts of elongated surgical instruments during insertion into a human or animal body, wherein the sealing element defines a longitudinal axis, is provided with an opening, which is variable in diameter and is oriented transversely or essentially transversely to the longitudinal axis and through which an instrument can be inserted, and comprises a flexible wall which is closed annularly, wherein the wall has a first and a second edge each closed upon itself and wherein the first edge limits the opening, such that all instruments currently available can be reliably sealed irrespective of the diameter of their instrument shaft it is suggested that the wall be foldable in a wave-like manner and in a sealing position be folded in a wave-like manner without kinks with fold lines extending in the direction towards the first edge in such a manner that the first edge defines a wave line which is located entirely on a cylindrical surface.

42 Claims, 8 Drawing Sheets

U.S. PATENT DOCUMENTS

| | | | |
|---|---|---|---|
| 5,127,626 A | 7/1992 | Hilal et al. | |
| 5,141,498 A | 8/1992 | Christian | |
| 5,174,613 A * | 12/1992 | Joug | 285/229 |
| 5,180,373 A | 1/1993 | Green et al. | |
| 5,197,955 A | 3/1993 | Stephens et al. | |
| 5,203,773 A | 4/1993 | Green | |
| 5,209,737 A | 5/1993 | Ritchart et al. | |
| 5,256,147 A | 10/1993 | Vidal et al. | |
| 5,261,891 A | 11/1993 | Brinkerhoff et al. | |
| 5,267,965 A | 12/1993 | Deniega | |
| 5,269,763 A | 12/1993 | Boehmer et al. | |
| 5,295,993 A | 3/1994 | Green | |
| 5,304,143 A | 4/1994 | Green et al. | |
| 5,308,336 A | 5/1994 | Hart et al. | |
| 5,314,417 A | 5/1994 | Stephens et al. | |
| 5,318,585 A | 6/1994 | Guy et al. | |
| 5,330,437 A * | 7/1994 | Durman | 604/167.04 |
| 5,338,305 A | 8/1994 | Plyley et al. | |
| 5,342,315 A | 8/1994 | Rowe et al. | |
| 5,342,382 A | 8/1994 | Brinkerhoff et al. | |
| 5,356,421 A | 10/1994 | Castro | |
| 5,385,553 A | 1/1995 | Hart et al. | |
| 5,387,197 A | 2/1995 | Smith et al. | |
| 5,399,167 A | 3/1995 | Deniega | |
| 5,405,328 A | 4/1995 | Vidal et al. | |
| 5,441,041 A | 8/1995 | Sauer et al. | |
| 5,462,532 A | 10/1995 | Gresl | |
| 5,467,762 A | 11/1995 | Sauer et al. | |
| 5,474,539 A | 12/1995 | Costa et al. | |
| 5,476,475 A | 12/1995 | Gadberry | |
| 5,486,190 A | 1/1996 | Green | |
| 5,522,833 A | 6/1996 | Stephens et al. | |
| 5,534,009 A | 7/1996 | Lander | |
| 5,569,160 A | 10/1996 | Sauer et al. | |
| 5,569,292 A | 10/1996 | Scwemberger et al. | |
| 5,584,850 A | 12/1996 | Hart et al. | |
| 5,603,702 A | 2/1997 | Smith et al. | |
| 5,609,604 A | 3/1997 | Schwemberger et al. | |
| 5,618,297 A | 4/1997 | Hart et al. | |
| 5,626,598 A | 5/1997 | Roth | |
| 5,658,236 A | 8/1997 | Sauer et al. | |
| 5,662,615 A | 9/1997 | Blake, III | |
| 5,669,885 A | 9/1997 | Smith | |
| 5,685,854 A | 11/1997 | Green et al. | |
| 5,690,663 A | 11/1997 | Stephens | |
| 5,690,664 A | 11/1997 | Sauer et al. | |
| 5,709,671 A | 1/1998 | Stephens et al. | |
| 5,752,938 A * | 5/1998 | Flatland et al. | 604/167.01 |
| 5,776,112 A | 7/1998 | Stephens et al. | |
| 5,803,919 A | 9/1998 | Hart et al. | |
| 5,807,338 A | 9/1998 | Smith et al. | |
| 5,817,061 A | 10/1998 | Goodwin et al. | |
| 5,851,216 A | 12/1998 | Allen | |
| 5,860,996 A | 1/1999 | Urban et al. | |
| 5,865,807 A | 2/1999 | Blake, III | |
| 5,879,332 A | 3/1999 | Schwemberger et al. | |
| 5,895,377 A | 4/1999 | Smith et al. | |
| 5,904,699 A | 5/1999 | Schwemberger et al. | |
| 5,906,595 A | 5/1999 | Powell et al. | |
| 5,916,232 A | 6/1999 | Hart | |
| 5,947,930 A | 9/1999 | Schwemberger et al. | |
| 5,980,493 A | 11/1999 | Smith et al. | |
| 5,989,224 A | 11/1999 | Exline et al. | |
| 5,997,510 A | 12/1999 | Schwemberger | |
| 6,004,326 A | 12/1999 | Castro et al. | |
| 6,197,041 B1 | 3/2001 | Shichman et al. | |
| 6,319,266 B1 | 11/2001 | Stellon et al. | |
| 6,497,716 B1 | 12/2002 | Green et al. | |
| 6,551,282 B1 | 4/2003 | Exline et al. | |
| 6,685,630 B2 | 2/2004 | Sauer et al. | |
| 6,702,787 B2 | 3/2004 | Racenet et al. | |
| 7,169,130 B2 | 1/2007 | Exline et al. | |
| 7,390,317 B2 | 6/2008 | Taylor et al. | |
| 7,731,694 B2 * | 6/2010 | Becker et al. | 604/167.06 |
| 2001/0042927 A1 * | 11/2001 | Rock | 261/79.1 |
| 2002/0026207 A1 | 2/2002 | Stellon et al. | |
| 2002/0156432 A1 | 10/2002 | Racenet et al. | |
| 2003/0195541 A1 | 10/2003 | Exline et al. | |
| 2004/0059297 A1 | 3/2004 | Racenet et al. | |
| 2004/0106942 A1 | 6/2004 | Taylor et al. | |
| 2004/0111060 A1 | 6/2004 | Racenet et al. | |
| 2004/0162531 A1 | 8/2004 | Wenchell | |
| 2004/0215209 A1 | 10/2004 | Almond et al. | |
| 2004/0230161 A1 | 11/2004 | Zeiner | |
| 2004/0260244 A1 | 12/2004 | Piechowicz et al. | |
| 2005/0033342 A1 | 2/2005 | Hart et al. | |
| 2005/0065543 A1 | 3/2005 | Kahle et al. | |
| 2005/0070943 A1 | 3/2005 | Hueil et al. | |
| 2005/0077688 A1 | 4/2005 | Voegele et al. | |
| 2005/0077689 A1 | 4/2005 | Hueil | |
| 2005/0107816 A1 | 5/2005 | Pingleton et al. | |
| 2005/0131349 A1 | 6/2005 | Albrecht et al. | |
| 2005/0251191 A1 | 11/2005 | Taylor et al. | |
| 2005/0288622 A1 | 12/2005 | Albrecht et al. | |
| 2005/0288634 A1 | 12/2005 | O'Heeron et al. | |
| 2006/0211992 A1 | 9/2006 | Prosek | |
| 2006/0217665 A1 | 9/2006 | Prosek | |
| 2006/0229654 A1 | 10/2006 | Voegele et al. | |
| 2006/0229655 A1 | 10/2006 | Voegele et al. | |
| 2007/0088277 A1 | 4/2007 | McGinley et al. | |
| 2007/0185453 A1 | 8/2007 | Michael et al. | |
| 2007/0255218 A1 | 11/2007 | Franer | |
| 2008/0249475 A1 | 10/2008 | Albrecht et al. | |

FOREIGN PATENT DOCUMENTS

| | | |
|---|---|---|
| DE | 43 03 026 | 8/1994 |
| DE | 692 22 688 | 3/1998 |
| DE | 696 02 111 | 4/1999 |
| DE | 693 23 750 | 10/1999 |
| DE | 102 14 552 | 10/2003 |
| DE | 20 2006 005 442 | 6/2006 |
| DE | 698 38 231 | 5/2008 |
| EP | 0 350 291 | 1/1990 |
| EP | 0 426 407 | 5/1991 |
| EP | 0 474 124 | 3/1992 |
| EP | 0 495 633 | 7/1992 |
| EP | 0 495 634 | 7/1992 |
| EP | 0 552 851 | 7/1993 |
| EP | 0 350 921 | 9/1994 |
| EP | 0 312 219 | 12/1994 |
| EP | 0 479 130 | 12/1994 |
| EP | 95/07663 | 3/1995 |
| EP | 0 520 296 | 4/1995 |
| EP | 0 494 520 | 9/1995 |
| EP | 0 511 676 | 7/1996 |
| EP | 0 499 457 | 5/1997 |
| EP | 0 567 142 | 7/1997 |
| EP | 0 517 248 | 10/1997 |
| EP | 0 617 924 | 10/1997 |
| EP | 0 642 764 | 12/1997 |
| EP | 0 630 213 | 1/1998 |
| EP | 0 594 687 | 4/1998 |
| EP | 0 600 921 | 5/1998 |
| EP | 0 649 634 | 9/1998 |
| EP | 0 697 838 | 9/1998 |
| EP | 0 630 619 | 10/1998 |
| EP | 0 648 096 | 11/1998 |
| EP | 0 696 459 | 11/1998 |
| EP | 0 768 063 | 2/1999 |
| EP | 0 652 730 | 3/1999 |
| EP | 0 724 864 | 4/1999 |
| EP | 0 591 851 | 6/1999 |
| EP | 0 684 016 | 12/1999 |

| | | | | | |
|---|---|---|---|---|---|
| EP | 0 768 064 | 12/1999 | WO | 93/01850 | 2/1993 |
| EP | 0 604 197 | 2/2000 | WO | 93/04632 | 3/1993 |
| EP | 0 614 384 | 2/2000 | WO | 93/04715 | 3/1993 |
| EP | 0 701 799 | 3/2000 | WO | 95/07663 | 3/1995 |
| EP | 0 716 862 | 8/2001 | WO | 95/15189 | 6/1995 |
| EP | 0 994 740 | 7/2003 | WO | 96/11640 | 4/1996 |
| EP | 0 785 756 | 9/2003 | WO | 98/50093 | 11/1998 |
| EP | 1 058 566 | 10/2003 | WO | 99/12481 | 3/1999 |
| EP | 0 769 278 | 1/2004 | WO | 99/52577 | 10/1999 |
| EP | 0 807 414 | 1/2004 | WO | 00/54679 | 9/2000 |
| EP | 1 402 827 | 3/2004 | WO | 01/89397 | 11/2001 |
| EP | 1 459 688 | 9/2004 | WO | 03/026512 | 4/2003 |
| EP | 1 350 476 | 4/2005 | WO | 03/043683 | 5/2003 |
| EP | 1 520 539 | 4/2005 | WO | 03/096879 | 11/2003 |
| EP | 1 520 541 | 4/2005 | WO | 0 867 150 | 11/2004 |
| EP | 0 873 721 | 12/2005 | WO | 2005/032348 | 4/2005 |
| EP | 1 625 863 | 2/2006 | WO | 2005/053783 | 6/2005 |
| EP | 1 671 596 | 6/2006 | WO | 2005/060844 | 7/2005 |
| EP | 1 707 136 | 10/2006 | WO | 2005/112799 | 12/2005 |
| EP | 1 707 137 | 10/2006 | WO | 2006/004652 | 1/2006 |
| EP | 1 520 544 | 6/2007 | WO | 2006/119197 | 11/2006 |
| EP | 1582158 | 12/2007 | WO | 2007/098495 | 8/2007 |
| EP | 1 889 580 | 2/2008 | WO | 2007/121425 | 10/2007 |
| GB | 1 466 242 | 3/1977 | | | |

* cited by examiner

SURGICAL SEALING ELEMENT, SURGICAL SEAL, AND SURGICAL SEALING SYSTEM

CROSS-REFERENCE TO RELATED APPLICATIONS

This application is a continuation of International application No. PCT/EP2007/052760 filed on Mar. 22, 2007, which claims priority to German application No. 10 2006 015 690.0 filed Mar. 27, 2006.

The present disclosure relates to the subject matter disclosed in International application No. PCT/EP2007/052760 of Mar. 22, 2007 and German application No. 10 2006 015 690.0 of Mar. 27, 2006, which are incorporated herein by reference in their entirety and for all purposes.

FIELD OF THE INVENTION

The present invention relates to surgical sealing elements generally, and more specifically to surgical sealing elements for a trocar and/or for sealing shafts of elongated surgical instruments during insertion into a human or animal body.

The present invention further relates to surgical seals generally, and more specifically to surgical seals for a trocar and/or for sealing shafts of elongated surgical instruments during insertion into a human or animal body.

Moreover, the present invention relates to surgical sealing systems generally, and more specifically to a surgical sealing system for the insertion of surgical instrument into a human or animal body, preferably along a longitudinal axis defined by the sealing systems.

BACKGROUND OF THE INVENTION

The present invention relates to a surgical sealing element, in particular, for a trocar and/or for sealing shafts of elongated surgical instruments during insertion into a human or animal body, wherein the sealing element defines a longitudinal axis, is provided with an opening, which is variable in diameter and oriented transversely or essentially transversely to the longitudinal axis and through which an instrument can be inserted, and comprises a flexible wall which is closed annularly, wherein the wall has a first and a second edge, each closed upon itself, and wherein the first edge limits the opening.

Furthermore, the present invention relates to a surgical seal, in particular, for a trocar and/or for sealing shafts of elongated surgical instruments during insertion into a human or animal body, wherein the seal comprises a first sealing element which defines a longitudinal axis, is provided with an opening, which is variable in diameter and oriented transversely or essentially transversely to the longitudinal axis and through which an instrument can be inserted, and comprises a first flexible wall which is closed annularly, wherein the first wall has a first and a second edge, each closed upon itself, and wherein the first edge limits the opening.

In addition, the present invention relates to a surgical sealing system for the insertion of surgical instruments into a human or animal body, preferably along a longitudinal axis defined by the sealing system, comprising a trocar which has an insertion opening and a surgical sealing element which closes the insertion opening at least partially and has an opening, the sealing element sealing the insertion opening during insertion of an instrument into the opening.

During endoscopic operations on the human or animal body, the body is often filled with a gas, which is physiologically safe and subject to a slight overpressure, for the purpose of expanding the operation site. So that the body can then be kept in a somewhat swollen state without having to replenish the gas to any excessively great extent, surgical sealing systems of the type described at the outset are, for example, used. They are normally designed in the form of a trocar which has two seals. One of the seals undertakes the sealing of the access point, i.e., an insertion opening of the trocar for as long as no instrument is inserted. An additional seal serves the purpose of sealing a shaft of the instrument inserted completely at its circumference in order to prevent any loss of gas as a result of the instruments inserted.

Since, for endoscopic procedures, instruments with different shaft diameters are used, seals with different inner diameters are normally utilized. In order to reliably seal instrument shafts with diameters in a range of 5 mm to 15 mm, different seals with inner diameters in a range of 3 mm to 12 mm are, for example, used. Seals with inner diameters of 3, 5, 10 and 12 mm inner diameter in the non-extended state are used, in particular. It is, therefore, necessary in many cases to provide several access points with trocars which have seals adapted to different instrument shaft diameters or also to replace the seals during a surgical procedure.

An object underlying the present invention is, therefore, to improve a surgical sealing element, a surgical seal as well as a surgical sealing system of the type described at the outset such that all instruments currently available can be reliably sealed irrespective of the diameter of their instrument shaft.

SUMMARY OF THE INVENTION

In a first aspect of the invention, a surgical sealing element, in particular, for a trocar and/or for sealing shafts of elongated surgical instruments during insertion into a human or animal body defines a longitudinal axis. The sealing element is provided with an opening variable in diameter and oriented transversely or essentially transversely to the longitudinal axis. An instrument being insertable through said opening. The sealing element comprises a flexible wall closed annularly. The wall has a first edge and a second edge each closed upon itself and the first edge limits the opening. The wall is foldable in a wave-like manner and in a sealing position is folded in a wave-like manner without kinks with fold lines extending in the direction towards the first edge in such a manner that the first edge defines a wave line located entirely on a cylindrical surface.

In a second aspect of the invention, a surgical seal, in particular, for a trocar and/or for sealing shafts of elongated surgical instruments during insertion into a human or animal body comprises a first sealing element defining a longitudinal axis. The seal is provided with an opening variable in diameter and oriented transversely or essentially transversely to the longitudinal axis. An instrument is insertable through said opening. The seal comprises a first flexible wall closed annularly, said first wall has a first and a second edge each closed upon itself and the first edge limits the opening. The first wall is foldable in a wave-like manner and in a sealing position is folded in a wave-like manner without kinks with fold lines extending in the direction towards the first edge in such a manner that a first edge defines a wave line located entirely on a cylindrical surface. A second sealing element identical or essentially identical to the first sealing element is provided and has a second wall also with a first and second edge. The first edge of the first sealing element is connected to the first edge of the second sealing element such that in the first sealing position a wave peak of a first wave line defined by the first edge of the first sealing element engages in a wave trough of a wave line defined by the first edge of the second sealing element.

In a third aspect of the invention, a surgical sealing system for the insertion of surgical instruments into a human or animal body, preferably along a longitudinal axis defined by the sealing system, comprises a trocar having an insertion opening and a surgical sealing element closing the insertion opening at least partially and having an opening. The surgical sealing element being designed for sealing shafts of elongated surgical instruments during insertion into the human or animal body. The sealing element defines a longitudinal axis and is provided with an opening variable in diameter and oriented transversely or essentially transversely to the longitudinal axis. An instrument being insertable through said opening. The sealing element comprises a flexible wall closed annularly. The wall has a first edge and a second edge each closed upon itself and the first edge limits the opening. The wall is foldable in a wave-like manner and in a sealing position is folded in wave-like manner without kinks with fold lines extending in the direction towards the first edge in such a manner that the first edge defines a wave-line located entirely on a cylindrical surface.

In a fourth aspect of the invention, a surgical sealing system for the insertion of surgical instruments into a human or animal body, preferably along a longitudinal axis defined by a sealing system, comprises a trocar having an insertion opening an a surgical seal closing the insertion opening at least partially at least and having an opening. Said surgical seal being designed for sealing shafts of elongated surgical instruments during insertion into the human or animal body. The seal comprises a first sealing element defining a longitudinal axis, is provided with an opening variable in diameter and oriented transversely or essentially transversely to the longitudinal axis. An instrument being insertable through said opening. The seal comprises a first flexible wall closed annularly, wherein the first wall has a first and a second edge each closed upon itself. The first edge limits the opening. The first wall is foldable in a wave-like manner and in a sealing position is folded in a wave-like manner without kinks with fold lines extending in the direction towards the first edge in such a manner that the first edge defines a wave line located entirely on a cylindrical surface. A second sealing element identical or essentially identical to the first sealing element is provided and has a second wall also with a first and second edge. The first edge of the first sealing element is connected to the first edge of the second sealing element such that in the first sealing position a wave peak of a first wave line defined by the first edge of the first sealing element engages in a wave trough of a wave line defined by the first edge of the second sealing element.

BRIEF DESCRIPTION OF THE DRAWINGS

The foregoing summary and the following description may be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalence of the claims and without departing from the invention.

The present invention relates to surgical sealing element, in particular, for a trocar and/or for sealing shafts of elongated surgical instruments during insertion into a human or animal body, wherein the sealing element defines a longitudinal axis, is provided with an opening variable in diameter and oriented transversely or essentially transversely to the longitudinal axis, an instrument being insertable through said opening, and comprises a flexible wall closed annularly, wherein the wall has a first edge and a second edge each closed upon itself and wherein the first edge limits the opening, wherein the wall is foldable in a wave-like manner and in a sealing position is folded in a wave-like manner without kinks with fold lines extending in the direction towards the first edge in such a manner that the first edge defines a wave line located entirely on a cylindrical surface.

Normally, the sealing function in surgical sealing elements is achieved via an annular elastic sealing lip. A maximum diameter of such a sealing lip is limited by the smallest cross section in the non-extended state. If such a sealing lip is stretched beyond its maximum possible diameter, this can cause damage to the seals as well as result in spreading forces which are too great and, consequently, in frictional forces on the instrument shaft which are too high. A sealing element designed in accordance with the invention is characterized by the fact that the first edge does not abut annularly around an instrument shaft, as in the case of the sealing lip described above, but rather describes a wave line on an instrument shaft. If an instrument with a larger diameter is inserted into the sealing element, the first edge is not elastically stretched, as in the case of the sealing lip described above, but rather the folded wall is successively unfolded. This results in the wave line defined by the first edge becoming smaller in its overall width in an axial direction which is determined by a distance between wave troughs and wave peaks of the wave line parallel to the longitudinal axis. A successive unfolding or smoothing of the folds, which, as in the case, for example, of a curtain, are designed to be free from kinks, therefore leads to a partial displacement of the first edge in an axial direction. The sealing of an instrument shaft can, in particular, be achieved with the improved sealing element without any elastic stretching of the first edge and the wall. Consequently, the spreading forces required are also reduced in the case of the improved sealing element in comparison with sealing elements known from the state of the art, likewise frictional forces during insertion of the instrument shaft into the opening. As a result of the wave line of the first edge, which is defined on account of the folding and extends, for example, sinusoidally or is composed of semicircular sections, a considerably greater range of instrument shaft diameters can, altogether, be reliably sealed, in particular, without any stretching of the first edge of the sealing element. In addition, the improved sealing element can already be of a funnel-shaped design on account of the folding or curtain-like gathering of the wall as suggested in a direction towards the first edge and so the insertion of an instrument is simplified and damage to the sealing element by the instrument to be inserted is avoided. In addition, wear and tear is reduced in comparison with conventional sealing elements which have a sealing lip since no stretching of the first edge is required in the case of the sealing element improved in accordance with the invention.

The cylindrical surface is preferably oriented concentrically to the longitudinal axis. It is then possible, in a simple manner, to insert cylindrical instrument shafts through the sealing element. Furthermore, a sealing element which is, altogether, rotationally symmetric or point symmetric can also be formed.

It is favorable when the sealing element, in a basic position, takes up a sealing position, in which the opening has altogether a minimum diameter. The opening can, in particular, be closed, i.e., a minimum diameter can also be 0 mm. In addition, the seal can, in the basic position, be designed such that the wall is folded or turned in in a wave-like manner in a direction towards the first edge, such as, for example, in the case of a curtain. As a result, the insertion of the instrument is made easier and damage to the sealing element avoided.

It is advantageous when the sealing element has, in the basic position, a wall which is folded in a wave-like manner without kinks in a direction towards the first edge and when the first edge defines a wave line which is located entirely on a cylindrical surface. Proceeding from this basic position, sealing of the instrument shaft can be achieved, during insertion of instrument shafts with a shaft diameter which is greater than the minimum inner diameter of the opening defined in the basic position, solely due to the fact that the wall is unfolded, without stretching it, for the purpose of widening the opening.

In accordance with a preferred embodiment of the invention, it may, in addition, be provided for the wave line to have wave peaks above a plane of opening of the opening extending at right angles to the longitudinal axis and wave troughs below the opening. In the case of conventional sealing elements with elastically extensible circular sealing lips, the sealing lip determines the plane of opening. In the case of the sealing element proposed in accordance with the invention, however, the first edge abuts on the instrument shaft partially above and partially below the plane of opening or is located on a virtual cylindrical surface.

An angular distance between two wave peaks is advantageously in an angular range of 25° to 50° in relation to the longitudinal axis. This means, in other words, that the wave line formed by the first edge comprises approximately six to 15 wave peaks and wave troughs, respectively. As a result, the unfolding of the wall proceeding from the first edge for the purpose of sealing instrument shafts with larger cross sections is made considerably easier.

It is favorable when the wall, in a plurality of sealing positions with respectively different diameters of the opening, is folded in the direction towards the first edge in a wave-like manner without any kinks in such a manner that the first edge defines a respective wave line which is located completely on a cylindrical surface. As a result, instrument shafts, which have, for example, a shaft narrowing or widening conically, can also be sealed since any optional shaft diameter can be sealed securely and reliably with such a sealing element according to the invention.

In accordance with a preferred embodiment of the invention, it may be provided for a diameter of the first edge to be, at the most, as great as a diameter of the second edge in a maximum opening position, in which the wall is free from folds and a diameter of the opening is at a maximum.

The wall can advantageously have the shape of a thin, cylindrical sleeve in the maximum opening position. As a result, one instrument shaft, the external diameter of which corresponds to the maximum diameter of the opening in the maximum opening position, can, at the most, be sealed.

In an alternative embodiment, it may, however, be advantageous when the wall has the shape of a flat circular ring in the maximum opening position.

This configuration can preferably be used in the case of sealing systems which may have only a minimum belly height.

Even if it is not, in principle, necessary, it is nevertheless favorable when the first edge is designed in the form of a sealing lip. Sealing of the first edge on an instrument shaft can, in particular, be improved further.

The first edge favorably bears a sealing lip. The sealing lip can be produced, for example, from a different material to the wall and, therefore, the first edge abut on an instrument shaft even better in order to seal the opening relative to the instrument shaft.

The construction of the sealing element is particularly simple when the sealing lip is designed in the form of a sealing ring or in the form of a bead circular or essentially circular in cross section. The sealing lip is preferably designed such that it likewise takes the form of a wave line in accordance with the first edge.

In order to achieve a particularly good sealing, the sealing lip is favorably produced from an elastic stretchable material. For example, the sealing lip can be designed in the form of an O ring integrally formed on the first edge or connected to it.

The wall and the sealing lip are advantageously produced from different materials. This makes it possible to design the wall so as to be preferably non-elastic, the sealing lip, on the other hand, to be elastic.

In accordance with a preferred embodiment of the invention, it may be provided for the sealing lip to be produced from a material which has a modulus of elasticity E which is greater than a modulus of elasticity of the material, from which the wall is produced, by a factor of $10^2$ to $10^5$. The sealing lip is, therefore, produced from a material which can be stretched more than the wall so that the sealing lip can abut elastically around an instrument shaft but the wall is practically non-elastic and cannot be stretched.

The wall is preferably produced from a non-elastic or essentially non-elastic material. This has the advantage, in particular, that materials can be used which allow the wall to permanently retain its shape predetermined by production, in particular, the shape which it has in the basic position.

The sealing element is preferably designed in one piece. This has the advantage that it can be produced in a single operating step.

It is favorable when the sealing element and/or the sealing lip are produced from at least one plastic material. The sealing element can then be produced particularly inexpensively.

The plastic material is advantageously rubber, silicone or a plastic material containing silicone and/or rubber. Using such a plastic material has the advantage, in particular, that the wall of the sealing element is sufficiently flexible to enable it to be laid in folds or to be gathered and to be unfolded again.

The sealing element will be particularly inexpensive, in addition, when it is produced by way of injection molding.

In accordance with a preferred embodiment of the invention, it may be provided for the second edge to be shaped and formed in every sealing position in such a manner that it is located completely in a plane extending transversely to the longitudinal axis. For example, the second edge can be of a circular or oval design. This means that the wall of the sealing element can be circular at one end and not folded whereas, at its other end forming the first edge, it has the shape of a wave line located on a cylindrical surface due to the folding provided.

In order to make it easier to fix the sealing element to a trocar, it is favorable when the second edge is shaped and formed in such a manner that it can be secured to a frame or to a holder of a trocar.

A non-flexible holder is preferably provided and the second edge held in the non-flexible holder. This has the advantage that the sealing element cannot be damaged when the sealing element is being connected to a trocar. In addition, the holder can be adapted in a desired manner to a receptacle of the trocar provided for it. The holder therefore forms, as it were, an interface between the sealing element and the trocar.

The construction of the sealing element will be particularly simple when the holder comprises a holding ring. This can, for example, be welded or glued to the second edge or in the area of the second edge. It would also be conceivable to connect the holder to the second edge in a clamping manner or secure it in the area of the second edge in a clamping manner.

The holder is preferably produced from a material different to that of the sealing element. This makes it possible to use, in particular, a stiffer material for the production of the holder than for the sealing element.

It is favorable when the holder is produced from a plastic material or a metal. A holder produced from a plastic material or a metal has the necessary stability to hold the sealing element securely, in particular, on a trocar.

Depending on the material, from which the sealing element is produced, the insertion of an instrument through the opening of the sealing element can be made more difficult. It is, therefore, advantageous when the sealing element is provided at least partially with a coating which reduces friction. The sealing element can, of course, also be provided completely with a coating which reduces friction and makes the insertion of an instrument through the opening of the sealing element easier.

In order not to impair the flexibility of the wall unnecessarily, it is favorable when the coating which reduces friction is applied at least partially to an inner side of the wall. Normally, losses due to friction occur only between an inner side of the wall and an instrument which is inserted through the opening of the sealing element. When only the inner side of the wall is provided with a coating which reduces friction, this has the advantage that such a coating must be provided only at the location where the coating is customarily required.

In accordance with a preferred embodiment of the invention, it may be provided for the coating which reduces friction to be produced from polytetrafluoroethylene (PTFE) or to contain polytetrafluoroethylene (PTFE). An inner side of the wall of the sealing element which is provided, in particular, with a coating of PTFE reduces losses due to friction during the insertion of instruments, the shaft diameters of which are greater than an inner diameter of the opening of the sealing element in the basic position.

In order to secure the sealing element in a simple manner, for example, in a clamping manner in a holder or on a trocar, it is advantageous when the second edge is of a bead-like design. The second edge projects preferably outwards in a bead-like manner, pointing radially away from the longitudinal axis.

It is advantageous when the second edge is turned over in the direction or essentially in the direction towards the first edge and when a sealing surface is formed in the area of the second edge which points away from the first edge. The second edge which is turned over makes it possible, in particular, to place a holding ring in the annular recess formed and to secure the sealing element between the holding ring and an inner wall of a trocar in a clamping manner. Furthermore, a sealing surface, which is preferably flat, is defined in a simple manner.

The sealing surface favorably extends in a plane transverse to a longitudinal axis of the sealing element. This allows the sealing element to be held, for example, against an annular sealing surface of a flange in order to seal an insertion opening of a trocar.

The sealing element may be connected in a simple manner to an additional component, for example, a trocar when a flange which points radially or essentially radially away from the longitudinal axis is formed, arranged or integrally formed in the area of the second edge. For example, the flange can be produced from a different material to the wall of the sealing element. It is favorable, in particular, when the flange is adhered or welded to the wall.

Moreover, the present invention relates to a surgical seal, in particular, for a trocar and/or for sealing shafts of elongated surgical instruments during insertion into a human or animal body, wherein the seal comprises a first sealing element defining a longitudinal axis, is provided with an opening variable in diameter and oriented transversely or essentially transversely to the longitudinal axis, an instrument being insertable through said opening, and comprises a first flexible wall closed annularly, wherein the first wall has a first and a second edge each closed upon itself and wherein the first edge limits the opening, wherein the first wall is foldable in a wave-like manner and in a sealing position is folded in a wave-like manner without kinks with fold lines extending in the direction towards the first edge in such a manner that the first edge defines a wave line located entirely on a cylindrical surface, wherein a second sealing element identical or essentially identical to the first sealing element is provided and has a second wall also with a first and second edge and wherein the first edge of the first sealing element is connected to the first edge of the second sealing element such that in the first sealing position a wave peak of a first wave line defined by the first edge of the first sealing element engages in a wave trough of a wave line defined by the first edge of the second sealing element.

Two sealing elements formed in such a manner may be connected completely along their first edges in a simple manner in that the two sealing elements are turned relative to one another about their common longitudinal axis through an angular distance which corresponds to a distance between two wave peaks of the wave line of one of the two first edges. For example, the two sealing elements can be adhered or welded to one another. It would also be conceivable to produce the surgical seal in one piece. The surgical seal developed further in accordance with the invention makes it possible to insert a surgical instrument from both sides and ensures sealing in relation to a surgical instrument in a desired manner. In addition, it is possible to avoid the first edge of a single sealing element from turning inside out during the insertion or withdrawal of an instrument, depending on whether it is inserted first of all through the opening formed by the first edge or through an opening formed by the second edge. The position of the first edge is, therefore, permanently determined in a simple manner. Furthermore, the stability of the seal is increased in comparison with a single sealing element, such as that described above, but without increasing frictional forces during the insertion of an instrument shaft through the opening since the wall need only be unfolded but not stretched. As a result, essentially the same forces are always required to increase the size of the sealing element during the insertion of the instrument shaft into the seal regardless of how large the diameter of an instrument shaft is.

The seal is preferably designed in the shape of a double funnel, i.e., the opening common to the two sealing elements forming the seal is smaller than an opening defined by the second edges and so a wall of the two sealing elements narrows in the direction towards the common opening.

According to a further, preferred embodiment of the invention, it may be provided for the first and/or the second sealing elements to be sealing elements of the type described above.

Furthermore, the invention relates to a surgical sealing system for the insertion of surgical instruments into a human or animal body, preferably along a longitudinal axis defined by the sealing system, comprising a trocar having an insertion opening and a surgical sealing element closing the insertion opening at least partially and having an opening, said surgical sealing element being designed for sealing shafts of elongated surgical instruments during insertion into the human or animal body, wherein the sealing element defines a longitudinal axis, is provided with an opening variable in diameter and oriented transversely or essentially transversely to the longitudinal axis, an instrument being insertable through said opening, and comprises a flexible wall closed annularly, wherein the wall has a first edge and a second edge each closed upon itself and wherein the first edge limits the opening, wherein the wall is foldable in a wave-like manner and in a sealing position is folded in a wave-like manner without kinks with fold lines extending in the direction towards the first edge in such a manner that the first edge defines a wave line located entirely on a cylindrical surface.

Moreover, the invention relates to a surgical sealing system for the insertion of surgical instruments into a human or animal body, preferably along a longitudinal axis defined by the sealing system, comprising a trocar having an insertion opening and a surgical seal closing the insertion opening at least partially and having an opening, said surgical seal being designed for sealing shafts of elongated surgical instruments during insertion into the human or animal body, wherein the seal comprises a first sealing element defining a longitudinal axis, is provided with an opening variable in diameter and oriented transversely or essentially transversely to the longitudinal axis, an instrument being insertable through said opening, and comprises a first flexible wall closed annularly, wherein the first wall has a first and a second edge each closed upon itself and wherein the first edge limits the opening, wherein the first wall is foldable in a wave-like manner and in a sealing position is folded in a wave-like manner without kinks with fold lines extending in the direction towards the first edge in such a manner that the first edge defines a wave line located entirely on a cylindrical surface, wherein a second sealing element identical or essentially identical to the first sealing element is provided and has a second wall also with a first and second edge and wherein the first edge of the first sealing element is connected to the first edge of the second sealing element such that in the first sealing position a wave peak of a first wave line defined by the first edge of the first sealing element engages in a wave trough of a wave line defined by the first edge of the second sealing element.

As explained in conjunction with the sealing elements described above as well as the seals described above, a plurality of elongated surgical instruments with optional shaft diameters can, in the case of a surgical sealing system suggested in accordance with the invention, be inserted into the sealing system and sealed by it.

The sealing element can advantageously be releasably connected to the trocar. This makes it possible to replace only the sealing element when this has been damaged or has aged.

The following description of preferred embodiments of the invention serves to explain the invention in greater detail in conjunction with the drawings.

Figure 1:
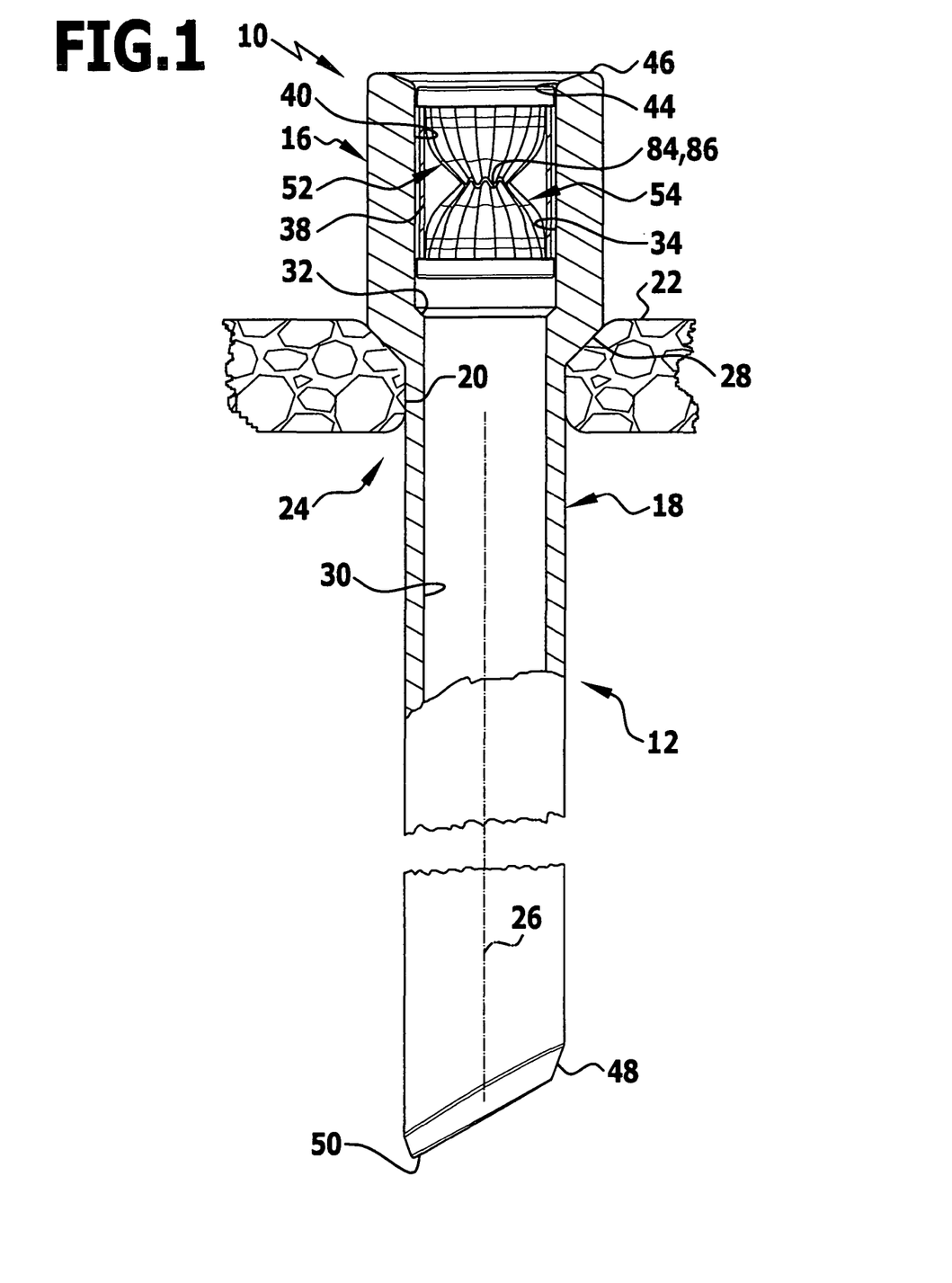
FIG. 1: shows a partially cutaway side view of a surgical sealing system according to the invention comprising a first embodiment of a sealing element according to the invention.

A surgical sealing system provided altogether with the reference numeral 10 is illustrated in FIG. 1 and comprises an elongated, sleeve-like trocar 12 with a surgical seal.

The trocar 12 comprises a sealing section 16 which forms a proximal end section of the trocar 12 and is adjoined on the distal side by an elongated insertion section 18 which can be inserted through an incision 20 in human or animal tissue, for example, skin 22 into a hollow space 24 of a human or animal body, for example, an abdominal area. An external diameter of the insertion section 18 is somewhat smaller than an external diameter of the sealing section 16 so that a ring-like annular surface 28 which is inclined relative to a longitudinal axis 26 of the trocar 12 through about 45° is formed in the transitional area between the two sections and points essentially in a distal direction. The annular surface 28 forms, in particular, a stop surface in order to prevent the sealing section 16 from being able to slide into the hollow space 24 through the incision 20. In a similar way, an inner diameter of a bore 30 extending concentrically to the longitudinal axis 26 through the entire trocar 12 widens in the transitional area from the insertion section 18 to the sealing section 16 in one step so that a second annular surface 32 is formed which is likewise inclined through approximately 45° in relation to the longitudinal axis 26 and points essentially in a proximal direction.

The bore 30 widening in one step in the area of the sealing section 16 forms a seal receptacle 34 for a surgical seal which is provided, altogether, with the reference numeral 36 and will be explained in greater detail in the following in conjunction with FIGS. 2 to 5. In addition, a holder 38 in the form of a holding sleeve, which is spaced somewhat from an inner wall 40 of the sealing section 16 and arranged concentrically to the longitudinal axis 26, is arranged in the seal receptacle 34 and so a gap 42 is formed between the holder 38 and the inner wall 40 at least in the area of the two ends. The holder 38 is preferably produced from a hard and sterilizable plastic material, such as, for example, polyether ether ketone (PEEK), or from a metal.

The seal 36 can be pushed into the seal receptacle 34 in a simple manner through an insertion opening 44 proceeding from a proximal end 46 of the trocar 12. After the seal 36 has been secured in the seal receptacle 34, an endoscopic instrument, which is not illustrated and has an elongated instrument shaft, can be introduced through the insertion opening 44. The seal 36 described in greater detail in the following ensures a fluid-tight sealing between the trocar 12 and a shaft 102 of the instrument inserted.

In order to make the insertion of the trocar 12 into a human or animal body easier and in order to avoid any damage to tissue, a distal end of the insertion section 18 is provided in a short section with an outer surface 48 which narrows conically in a distal direction and, in addition, is inclined somewhat relative to the longitudinal axis so that an annular end face 50 of the insertion section 18 points in a distal direction at an angle of approximately 30°.

The construction of the seal 36 will be explained in greater detail in the following in conjunction with FIGS. 2 to 5.

Figure 2:
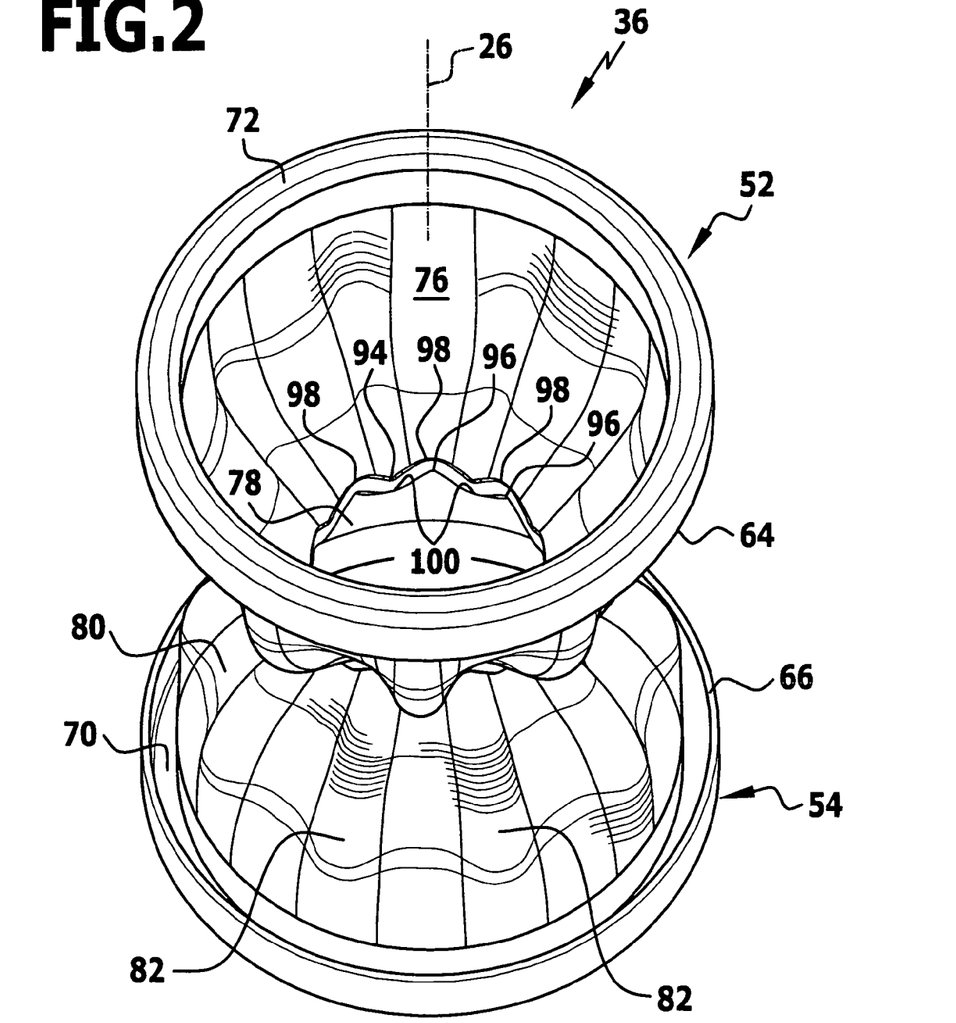
FIG. 2: shows a perspective view of the first embodiment of a sealing element according to the invention from FIG. 1.
Figure 3:
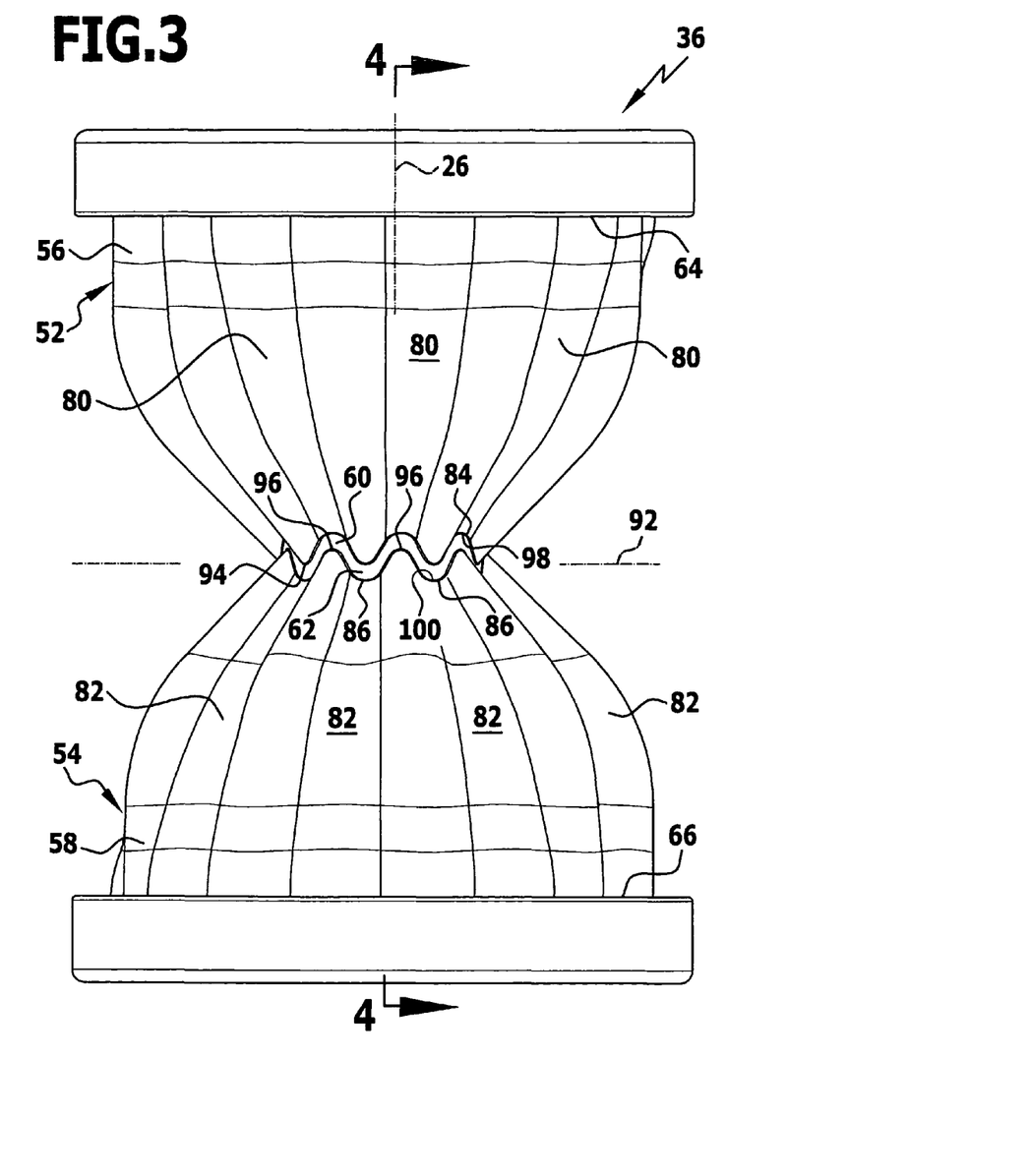
FIG. 3: shows a side view of the sealing element from FIG. 2.
Figure 4:
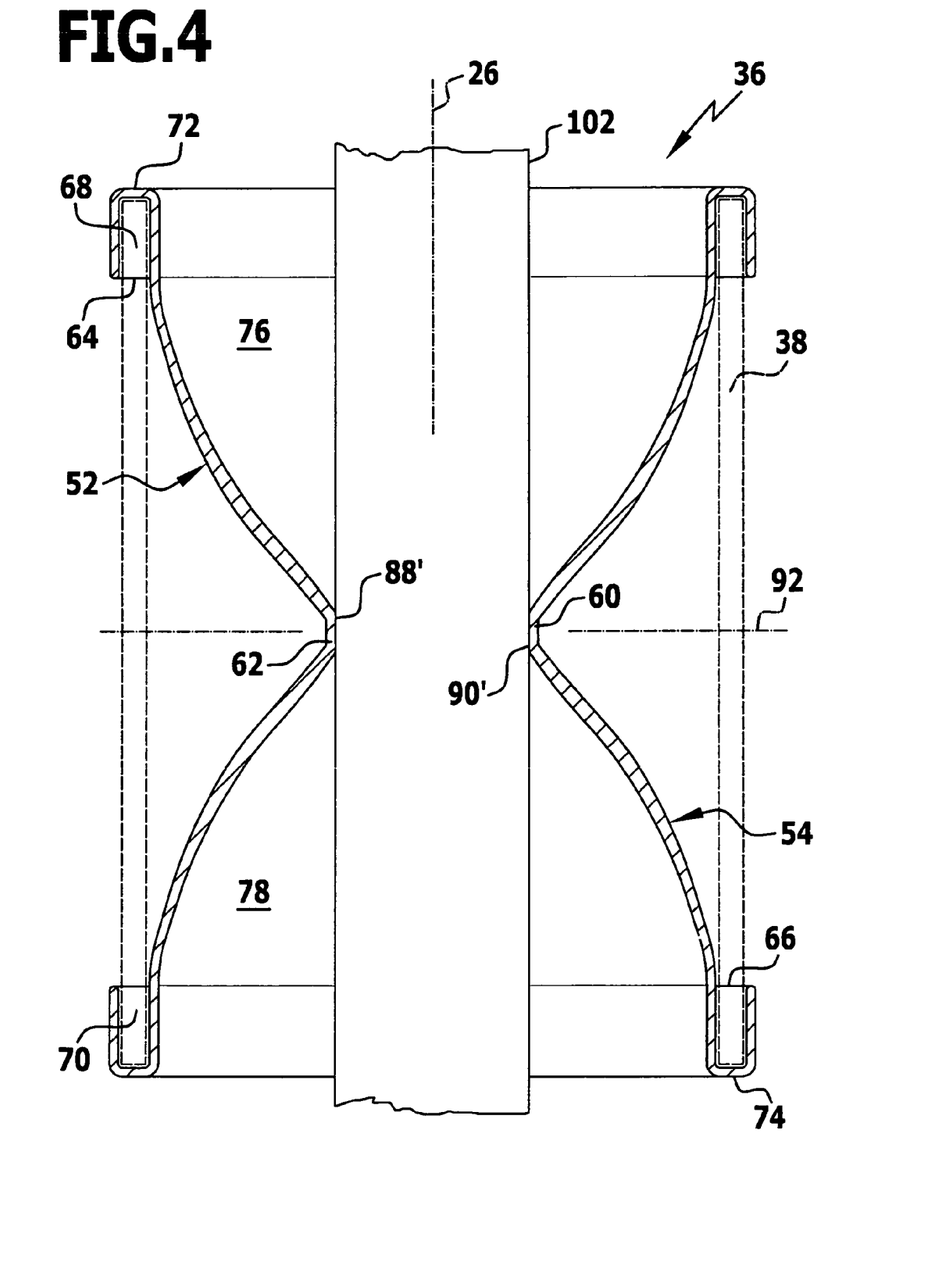
FIG. 4: shows a sectional view of the sealing element from FIG. 3 along line 4-4 with an instrument shaft inserted.

The seal 36 is formed by two identical sealing elements 52 and 54 which are connected to one another or designed in one piece in order to form the seal 36. Each sealing element 52 and 54, respectively, has an annular flexible wall 56 and 58, respectively, which is closed upon itself and has a first edge 60 and 62, respectively, as well as a second edge 64 and 66, respectively. The first edges 60 and 62 each form a first end of the sealing elements 52 and 54, the second edges 64 and 66 a second end of the sealing elements 52 and 54. The second edges 64 and 66 are turned over outwards so that they point essentially in the direction towards the first edges 60 and 62, respectively, and form annular grooves 68 and 70 which are open essentially in the direction towards the first edges 60 and 62, respectively, and into which the sleeve-like holder 38 on the trocar 12 can be pushed. The second edges 64 and 66 are preferably of a circular design and located in a plane transverse to the longitudinal axis 26. As a result of the second edges 64 and 66 being turned over, a section of the inner sides 76 and 78 of the walls 56 and 58 forms circular sealing surfaces 72 and 74 which each point away from the first edge 60 and 62, respectively, and the surface normal of which extends parallel to the longitudinal axis 26.

The walls 56 and 58 are circular in cross section in the area of the sealing surfaces 72 and 74. In the direction towards the first edges 60 and 62 they are folded in a wave-like manner without kinks with fold lines extending in the direction towards the first edges 60 and 62. In other words, the walls 56 and 58 are gathered like curtains in the direction towards the first edges 60 and 62 so that the first edges 60 and 62 define, in a side view, a wave line 84 and 86, respectively. In the side view, the first edges 60 and 62 are, therefore, of a wave-like design, namely approximately sinusoidal. On the other hand, in a plan view they each limit a circular opening 88 and 90, respectively, in the direction of the longitudinal axis 26. The wave lines 84 and 86 extend in such a manner that in a plane of opening 92 extending at right angles to the longitudinal axis 26 wave peaks 94 and 96 extend on a different side of the plane of opening 92 when viewed from the respective second edge 64 and 66, respectively, wave troughs 98 and 100 of the wave lines 84 and 86, on the other hand, on the same side as the second edges 64 and 66 in relation to the plane of opening 92.

Each of the two sealing elements 52 and 54 is, therefore, essentially in the shape of a funnel and narrows in an inner diameter in the direction towards the first edge 60 and 62. The first edges 60 and 62, although they each define a wave line 84 and 86, respectively, in axial direction, as illustrated in the side view in FIG. 3, are, however, located completely on a cylindrical surface concentrically surrounding the longitudinal axis 26. This results, altogether, in a circular opening 88, as illustrated in the plan view in FIG. 5a.

As illustrated in FIGS. 1 to 4, the seal 36 is formed by the two sealing elements 42 and 44 in such a manner that the first edges 60 and 62 are connected to one another, which is achieved in that the two sealing elements 52 and 54 are turned relative to one another about the longitudinal axis through half a distance between two wave peaks 94 and 96, respectively, or two wave troughs 98 and 100, respectively, so that the wave peaks 94 of the sealing element 52 engage in the wave troughs 100 of the sealing element 54 and the wave peaks 96 of the second sealing element 54 in the wave troughs 98 of the sealing element 52. As a result, the first edges 60 and 62 abut completely on one another and define a common wave line 84 and 86, respectively. The seal 36 is, therefore, designed altogether in the shape of a double funnel and narrows in the direction towards the plane of opening 92. The annular grooves 68 and 70 point towards one another and so the seal is held on the holder 38 which is in the shape of a cylindrical sleeve and engages on both sides in the annular grooves 68 and 70, as illustrated in FIG. 4. The first edges 60 and 62 connected to one another therefore form a type of sealing lip of the seal 36 which, in a side view, extends in the form of a wave line 84 and 86, respectively, but is located completely on a cylindrical surface and can, therefore, sealingly enclose an instrument, which is circular in cross section, or a shaft 102 completely.

Figure 5A:
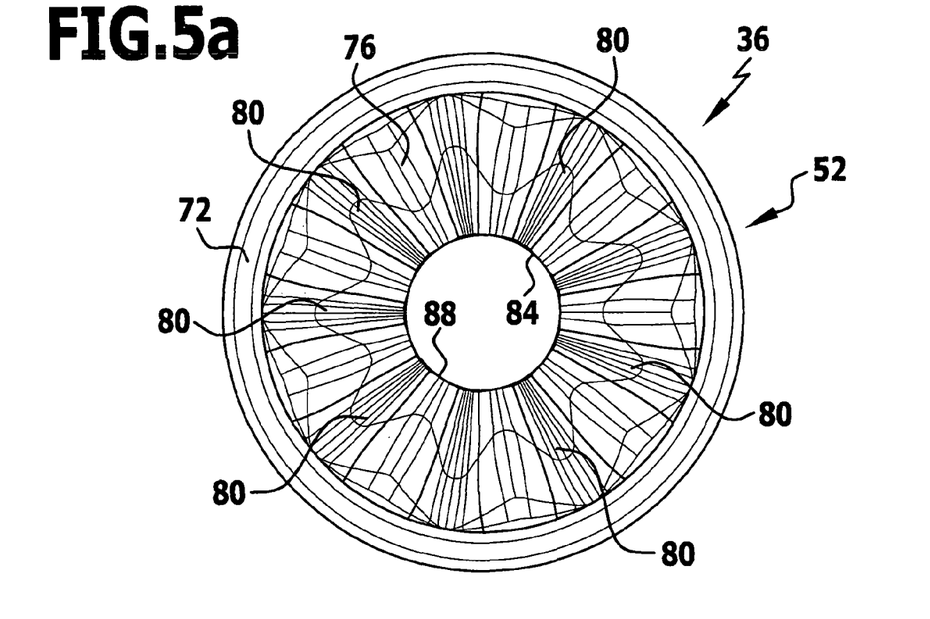
FIG. 5a: shows a plan view of a sealing element according to the invention in the basic position.
Figure 5B:
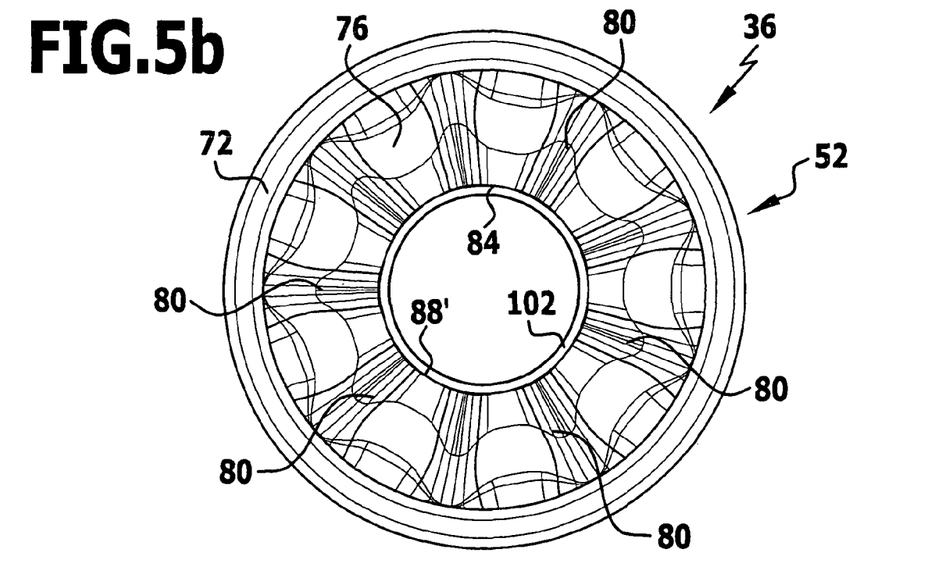
FIG. 5b: shows a plan view of the sealing element from FIG. 5a in a sealing position with an opening increased in size in comparison with the basic opening.

In principle, it would be conceivable to produce the walls 56 and 58 from an elastically stretchable material. This is, however, not required for the present invention. It is sufficient when the wall is produced from a flexible material. It is then possible to insert a surgical instrument with an elongated, cylindrical shaft 102 into the seal 36 and seal it. If an external diameter of the shaft 102 is greater than the inner diameter of the openings 88 and 90 in the basic position, the shaft 102 causes an unfolding of the walls 56 and 58 but the first edges 60 and 62 still abut completely on the shaft 102 since they are located entirely on a cylindrical surface in every sealing position. A change in the folding as a result of the shaft 102 inserted is illustrated in FIG. 5b. The opening 88' widened in diameter is still circular, wherein the first edges 60 and 62 still define a wave line 84 and 86, respectively. However, the wave peaks 94 and 96 as well as the wave troughs 98 and 100 are no longer as high as in the case of the seal 36 which is in the basic position. The sealing of the instruments is, therefore, brought about only by an unfolding of the walls 56 and 58 but not by any stretching of the first edges 60 and 62 or of the walls 56 and 58. This has the advantage that during the insertion of an instrument with a shaft 102 which is greater in diameter than an inner diameter of the opening 88 of the seal 36 in the basic position, less force need be used to insert the instrument into the trocar 12 than is the case for conventional trocars with seals which are based on the principle of elastic stretching of a sealing lip or of a sealing edge.

The sealing elements 52 and 54 suggested in accordance with the invention and, therefore, the seal 36, as well, make it possible in the extreme case to insert an instrument with an external diameter which corresponds to an inner diameter of the sealing elements 52 and 54 in the area of the second edges 64 and 66, respectively, which is turned over, since the first edges 60 and 62 are preferably folded such that they no longer define a wave line 84 and 86, respectively, in the unfolded or ungathered state but rather a circular line which surrounds the longitudinal axis 26 concentrically. This also means, however, that a distance between the plane of opening 92 and the sealing surfaces 72 and 74 will alter as a consequence of the walls 56 and 58 of the sealing elements 52 and 54 unfolding. A minimum distance is predetermined in the basic position, in which the opening 88 has a minimum inner diameter. In a position of the seal 36 unfolded to a maximum, the distances of the sealing surfaces 72 and 74 from the plane of opening 92 are at a maximum. This also means, however, that the seal 36 should preferably be held on the trocar 12 in such a manner that the two sealing surfaces 72 and 74 are held so as to be movable relative to one another in an axial direction.

As a result of the design of the seal 36 in the shape of a double funnel, shafts 102 can be inserted into the seal 36 from both sides. Any withdrawal of the shaft 102 out of the seal 36 does not lead to any undesired turning inside out of the first edges 60 and 62.

The seal 36 is preferably designed in one piece and produced from a plastic material as a result of injection molding. Rubber, silicones or plastic materials containing silicones and/or rubber are particularly suitable as plastic materials and can be optionally provided with a coating consisting of polytetrafluoroethylene (PTFE) which reduces friction.

Figure 6:
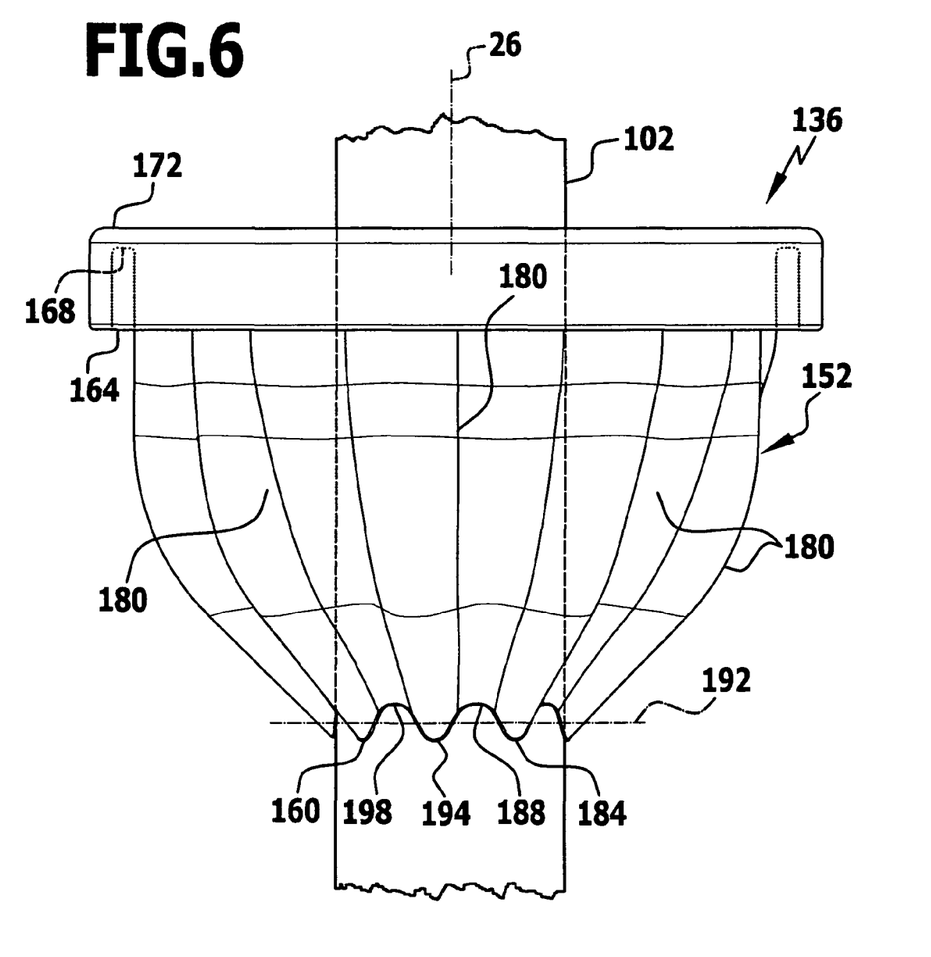
FIG. 6: shows a side view of a second embodiment of a sealing element according to the invention with an instrument shaft inserted.

A second embodiment of a seal provided altogether with the reference numeral 136 is illustrated in FIG. 6 with a sealed instrument shaft 102 inserted. The seal 136 is formed from only a single sealing element 152 which is of an identical design to the sealing element 52 and so identical parts of the sealing element 152 are provided with reference numerals which have the same two end numerals as the corresponding reference numerals of the sealing element 52. As a result of the first edge 160 being folded or gathered in a wave-like manner without any kinks, a wave line 184, which abuts on the shaft 102 circular in cross section, i.e., on a cylindrical surface and defines a circular opening 188 in a plan view, as can be seen in FIG. 5b, results in the side view illustrated in FIG. 6. The wall 156 of the sealing element 152 is, altogether, laid in folds like the wall 56 of the sealing element 52. The second edge 164 is likewise turned over in the direction towards the first edge 160 so that an annular groove 168 is formed, in which a holding ring or a holding sleeve can, for example, engage in order to secure the sealing element 152 on a trocar.

The wave line 184 forms, as can be seen in FIG. 6 in the side view, wave peaks 194 and wave troughs 198 in relation to a central plane of opening 192. It is not necessary in the case of the sealing element 152, as well, to produce the wall 156 from an elastically stretchable material; it is sufficient when the wall 156 is produced from a flexible material which allows the opening 188 to be altered by unfolding and, therefore, by reducing a height and depth of the wave peaks 194 and the wave troughs 198, respectively.

The sealing element 152 can be produced from the same materials as the seal 36.

In addition, it is possible to form a sealing lip, which preferably points in a radial direction in the direction towards the longitudinal axis 26, in the area of the first edges 60 and 62 of the seal 36 or of the first edge 160 of the seal 136. The sealing lip can be integrally formed on the respective seal 36 and 136, respectively, in one piece but can also consist of a different material, in particular, also of an elastically stretchable material and be adhered or welded to the first edge 60 and 62, respectively, or 160.

Figure 7:
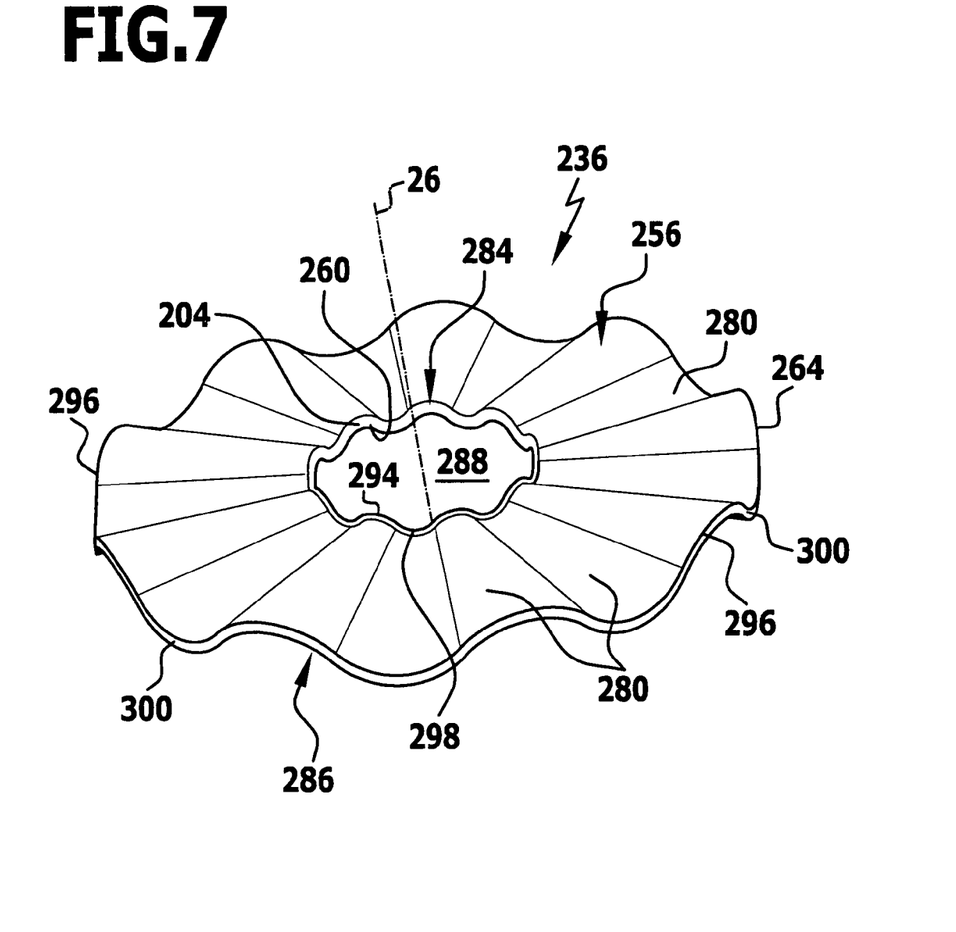
FIG. 7: shows a perspective view of a third embodiment of a sealing element according to the invention.

A third embodiment of a seal according to the invention is illustrated in FIG. 7 and provided, altogether, with the reference numeral 236. It likewise comprises a first edge 260 as well as a second edge 264. The first edge 260 defines an opening which is circular in the plan view but in a side view is shaped in the form of a wave line similar to the first edges 60, 62 and 160 of the seals 36 and 136. The wave line is located completely on a cylindrical surface extending concentrically around the longitudinal axis 26. The second edge 264 is likewise shaped in the form of a wave line and is likewise located, in contrast to the second edges 64 and 66 of the seal 36, on a cylindrical surface which surrounds the longitudinal axis 26 concentrically and the diameter of which corresponds, however, to about three times the diameter of the cylindrical surface, on which the first edge 260 is located. The wall 256 is consequently located essentially in a plane, the so-called plane of opening, above which wave peaks 294 of the first edge 260 and wave peaks 296 of the second edge 264 are located. The wave troughs 298 of the first edge 260 as well as the wave troughs 300 of the second edge 264 are located beneath the plane of opening. The wall 256, which is produced from a preferably non-elastic but flexible material, is therefore laid altogether in kink-free folds which define fold lines 280 which extend in a radial direction away from the longitudinal axis 26. The wall 156, in a completely unfolded sealing position, takes on the shape of a flat circular ring.

In the case of the seal 236 illustrated in FIG. 7, a bead-like sealing lip 204 is integrally formed on the first edge 260, in addition. The provision of a sealing lip 204 for the seal 236 is, however, optional and not necessary on account of the principle of the sealing of a cylindrical shaft already described above in greater detail. The sealing lip 204 is preferably produced from an elastic material and projects from the first edge 260 in a radial direction pointing towards the longitudinal axis 26. The sealing lip 204 can be injection molded, welded or adhered to the first edge 260.

Figure 8:
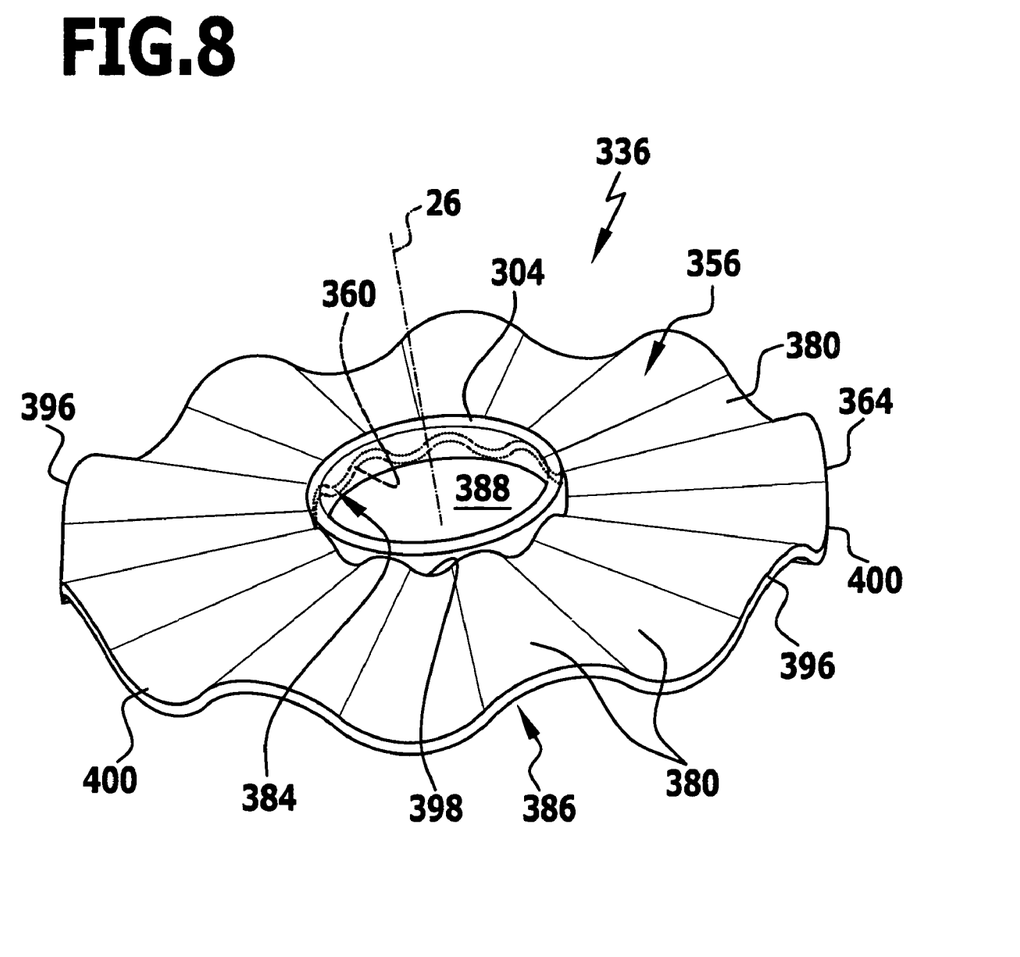
FIG. 8: shows a perspective view of a fourth embodiment of a sealing element according to the invention.

A fourth embodiment of a seal according to the invention is provided in FIG. 8 altogether with the reference numeral 336. It is constructed essentially identically to the seal 236 and so parts of the seal 336 which correspond to parts of the seal 236 are provided with reference numerals which have the same two end numerals.

The seal 336 is, therefore, like the seal 236, of a circular design in a plan view in a basic position, in which a first edge 360 defines a minimum opening 388 with a minimum inner diameter so that a wall 356 of the seal 336 essentially defines a plane, the so-called plane of opening which extends transversely to the longitudinal axis of the seal 336. Wave peaks 394 of the first edge 360 and wave peaks 396 of the second edge 364 rise above the plane of opening, wave troughs 398 of the first edge 360 and wave troughs 400 of the second edge 364 lie below the plane of opening. Therefore, the wall 356 which is laid or gathered in kink-free folds likewise defines fold lines 380 which extend in a radial direction away from the longitudinal axis 26. The seal 336 is provided with a sealing lip 304 which is designed in the form of a cylindrical ring consisting of an elastic material. A height of the sealing lip 304 in an axial direction is somewhat greater than a distance between the wave peaks 394 and the wave troughs 396 of the first edge 360.

The functional principle of the seals 236 and 336 will be explained in greater detail in the following.

Instruments with, in particular, a cylindrical shaft can be inserted through the openings 288 and 388. If an external diameter of an instrument is greater than the inner diameter of the openings 288 and 388 of the seals 236 and 336 in a basic position, in which the openings 288 and 388 have their smallest inner diameter, sealing of the instrument shaft will be brought about in that the folding of the walls 256 and 356 is smoothed out in order to widen the openings 288 and 388 in their inner diameter. For this purpose, no stretching of the wall 256 and 356, respectively, is required. As in the case of the embodiments in FIGS. 7 and 8, sealing lips 204 and 304 can, however, be provided and these can improve the sealing properties of the seals 236 and 336 even more, depending on which type of instrument is intended to be sealed with the seals 236 and 336.

Furthermore, the seals 236 and 336 can be produced from the same material or the same materials as the seals 36 and 136. The seals 236 and 336 can also, of course, be coated with a coating which reduces friction, for example, a slide coating consisting of polytetrafluoroethylene (PTFE). The sealing lip 304 can be injection molded or adhered to the first edge 360. Furthermore, it would also be possible to weld the sealing lip 304 to the first edge 260.

The seals 236 and 336 can be secured to a corresponding receptacle of a trocar with their second edges 264 and 364 in a manner not illustrated in detail in order to form a surgical sealing system.

The property common to all the embodiments of seals according to the invention as described above is the fact that an opening is achieved by unfolding or reducing folding of a wall of the seal, wherein a complete abutment of a first edge of the seal on the instrument shaft is nevertheless ensured.

The invention claimed is:

1. Surgical sealing element, in particular, for a trocar and/or for sealing shafts of elongated surgical instruments during insertion into a human or animal body, wherein the sealing element defines a longitudinal axis, is provided with an opening variable in diameter and oriented transversely or essentially transversely to the longitudinal axis, an instrument being insertable through said opening, and comprises a flexible wall closed annularly, wherein the wall has a first edge and a second edge each closed upon itself and wherein the first edge limits the opening, wherein the wall is foldable in a wave-like manner and in a sealing position is folded in a wave-like manner without kinks with fold lines extending in the direction towards the first edge in such a manner that the first edge defines a wave line located entirely on a cylindrical surface.

2. Surgical sealing element as defined in claim 1, wherein the cylindrical surface is oriented concentrically to the longitudinal axis.

3. Surgical sealing element as defined in claim 1, wherein in a basic position the sealing element takes up a sealing position, the opening having a minimum diameter in said position.

4. Surgical sealing element as defined in claim 3, wherein the sealing element has in the basic position a wall folded in the direction towards the first edge in a wave-like manner without kinks and wherein the first edge defines a wave line located entirely on a cylindrical surface.

5. Surgical sealing element as defined in claim 1, wherein the wave line has wave peaks above a plane of opening of the opening extending at right angles to the longitudinal axis and wave troughs below the plane of opening.

6. Surgical sealing element as defined in claim 5, wherein an angular distance between two wave peaks is in an angular range of 25° to 50° in relation to the longitudinal axis.

7. Surgical sealing element as defined in claim 1, wherein in a plurality of sealing positions with respectively different diameters of the opening the wall is folded in the direction of the first edge in a wave-like manner without kinks in such a manner that the first edge defines a respective wave line located completely on a cylindrical surface.

8. Surgical sealing element as defined in claim 1, wherein in a maximum opening position, the wall being free from folds and a diameter of the opening being at a maximum in said position, a diameter of the first edge is at the most as great as a diameter of the second edge.

9. Surgical sealing element as defined in claim 8, wherein the wall has the shape of a thin cylindrical sleeve in the maximum opening position.

10. Surgical sealing element as defined in claim 8, wherein the wall has the shape of a flat circular ring in the maximum opening position.

11. Surgical sealing element as defined in claim 1, wherein the first edge is designed in the form of a sealing lip.

12. Surgical sealing element as defined in claim 11, wherein the sealing lip is designed in the form of a sealing ring or in the form of a bead circular or essentially circular in cross section.

13. Surgical sealing element as defined in claim 11, wherein the sealing lip is produced from an elastic stretchable material.

14. Surgical sealing element as defined in claim 11, wherein the wall and the sealing lip are produced from different materials.

15. Surgical sealing element as defined in claim 11, wherein the sealing lip is produced from a material having a modulus of elasticity E greater by a factor of $10^2$ to $10^5$ than a modulus of elasticity of the material used to produce the wall.

16. Surgical sealing element as defined in claim 1, wherein the first edge bears a sealing lip.

17. Surgical sealing element as defined in claim 1, wherein the wall is produced from a non-elastic or essentially non-elastic material.

18. Surgical sealing element as defined in claim 1, wherein the sealing element is designed in one piece.

19. Surgical sealing element as defined in claim 1, wherein the sealing element and/or the sealing lip is produced from at least one plastic material.

20. Surgical sealing element as defined in claim 19, wherein the plastic material is rubber, silicone or a plastic material containing silicone and/or rubber.

21. Surgical sealing element as defined in claim 1, wherein the sealing element is produced by way of injection molding.

22. Surgical sealing element as defined in claim 1, wherein the second edge is shaped and formed in every sealing position in such a manner that it is located completely in a plane extending transversely to the longitudinal axis.

23. Surgical sealing element as defined in claim 1, wherein the second edge is shaped and formed in such a manner that it is adapted to be secured to a frame or a holder of a trocar.

24. Surgical sealing element as defined in claim 1, wherein a non-flexible holder is provided and that the second edge is held in or on the non-flexible holder.

25. Surgical sealing element as defined in claim 24, wherein the holder comprises a holding ring.

26. Surgical sealing element as defined in claim 24, wherein the holder is produced from a material different to that of the sealing element.

27. Surgical sealing element as defined in claim 26, wherein the holder is produced from a plastic material or a metal.

28. Surgical sealing element as defined in claim 1, wherein the sealing element is provided at least partially with a coating reducing friction.

29. Surgical sealing element as defined in claim 28, wherein the coating reducing friction is applied at least partially to an inner side of the wall.

30. Surgical sealing element as defined in claim 28, wherein the coating reducing friction is produced from polytetrafluoroethylene (PTFE) or contains polytetrafluoroethylene (PTFE).

31. Surgical sealing element as defined in claim 1, wherein the second edge is of a bead-like design.

32. Surgical sealing element as defined in claim 1, wherein the second edge is turned over in the direction or essentially in the direction towards the first edge and wherein a sealing surface is formed in the area of the second edge, said sealing surface pointing away from the first edge.

33. Surgical sealing element as defined in claim 32, wherein the sealing surface extends in a plane transverse to a longitudinal axis of the sealing element.

34. Surgical sealing element as defined in claim 1, wherein a flange pointing radially or essentially radially away from the longitudinal axis is formed, arranged or integrally formed in the area of the second edge.

35. Surgical seal, in particular, for a trocar and/or for sealing shafts of elongated surgical instruments during insertion into a human or animal body, wherein the seal comprises a first sealing element defining a longitudinal axis, is provided with an opening variable in diameter and oriented transversely or essentially transversely to the longitudinal axis, an instrument being insertable through said opening, and comprises a first flexible wall closed annularly, wherein the first wall has a first and a second edge each closed upon itself and wherein the first edge limits the opening, wherein the first wall is foldable in a wave-like manner and in a sealing position is folded in a wave-like manner without kinks with fold lines extending in the direction towards the first edge in such a manner that the first edge defines a wave line located entirely on a cylindrical surface, wherein a second sealing element identical or essentially identical to the first sealing element is provided and has a second wall also with a first and second edge and wherein the first edge of the first sealing element is connected to the first edge of the second sealing element such that in the first sealing position a wave peak of a first wave line defined by the first edge of the first sealing element engages in a wave trough of a wave line defined by the first edge of the second sealing element.

36. Surgical seal as defined in claim 35, wherein the wave line has wave peaks above a plane of opening of the opening extending at right angles to the longitudinal axis and wave troughs below the plane of opening.

37. Surgical sealing system for the insertion of surgical instruments into a human or animal body, preferably along a longitudinal axis defined by the sealing system, comprising a trocar having an insertion opening and a surgical sealing element closing the insertion opening at least partially and having an opening, said surgical sealing element being designed for sealing shafts of elongated surgical instruments during insertion into the human or animal body, wherein the sealing element defines a longitudinal axis, is provided with an opening variable in diameter and oriented transversely or essentially transversely to the longitudinal axis, an instrument being insertable through said opening, and comprises a flexible wall closed annularly, wherein the wall has a first edge and a second edge each closed upon itself and wherein the first edge limits the opening, wherein the wall is foldable in a wave-like manner and in a sealing position is folded in a wave-like manner without kinks with fold lines extending in the direction towards the first edge in such a manner that the first edge defines a wave line located entirely on a cylindrical surface.

38. Surgical sealing system as defined in claim 37, wherein the wave line has wave peaks above a plane of opening of the opening extending at right angles to the longitudinal axis and wave troughs below the plane of opening.

39. Surgical sealing system as defined in claim 37, wherein the sealing element is releasably connectable to the trocar.

40. Surgical sealing system for the insertion of surgical instruments into a human or animal body, preferably along a longitudinal axis defined by the sealing system, comprising a trocar having an insertion opening and a surgical seal closing the insertion opening at least partially and having an opening, said surgical seal being designed for sealing shafts of elongated surgical instruments during insertion into the human or animal body, wherein the seal comprises a first sealing element defining a longitudinal axis, is provided with an opening variable in diameter and oriented transversely or essentially transversely to the longitudinal axis, an instrument being insertable through said opening, and comprises a first flexible wall closed annularly, wherein the first wall has a first and a second edge each closed upon itself and wherein the first edge limits the opening, wherein the first wall is foldable in a wave-like manner and in a sealing position is folded in a wave-like manner without kinks with fold lines extending in the direction towards the first edge in such a manner that the first edge defines a wave line located entirely on a cylindrical surface, wherein a second sealing element identical or essentially identical to the first sealing element is provided and has a second wall also with a first and second edge and wherein the first edge of the first sealing element is connected to the first edge of the second sealing element such that in the first sealing position a wave peak of a first wave line defined by the first edge of the first sealing element engages in a wave trough of a wave line defined by the first edge of the second sealing element.

41. Surgical sealing system as defined in claim 40, wherein the wave line has wave peaks above a plane of opening of the opening extending at right angles to the longitudinal axis and wave troughs below the plane of opening.

42. Surgical sealing system as defined in claim 40, wherein the sealing element is releasably connectable to the trocar.

* * * * *